United States Patent [19]

Harman, III

[11] 4,410,409
[45] Oct. 18, 1983

[54] AMPEROMETRIC GAS SENSOR, CATHODE ASSEMBLY THEREFOR AND METHOD OF MAKING SAID CATHODE ASSEMBLY

[75] Inventor: John N. Harman, III, Placentia, Calif.

[73] Assignee: Beckman Instruments, Inc., Fullerton, Calif.

[21] Appl. No.: 335,019

[22] Filed: Dec. 28, 1981

[51] Int. Cl.³ .................. G01N 27/30; G01N 27/54
[52] U.S. Cl. ................................ 204/415; 29/592 R
[58] Field of Search .................. 204/195 P, 1 P; 128/635; 29/592 R

[56] References Cited

U.S. PATENT DOCUMENTS 3,518,179  6/1970  Bleak et al. ................. 204/195 P
4,268,370  5/1981  Neti ........................... 204/195 P Primary Examiner—G. L. Kaplan
Attorney, Agent, or Firm—Robert J. Steinmeyer; Paul R. Harder; Edward C. Jason

[57] ABSTRACT

An improved electrode assembly for use in amperometric gas sensors. A portion of the interior of the electrode assembly that is adjacent to the electrode is filled with an electrochemically inert water-repellant fluid. Once the fluid is in place, a fluid barrier is inserted to cover the fluid and to serve as a foundation for the introduction of a sealing compound. A pressure relief structure, such as a gas bubble, may be provided within the fluid to relieve the pressures incident to the thermal expansion and contraction of the electrode assembly. Because of the water repellancy of the fluid, the electrolyte solution which surrounds the electrode assembly is prevented from migrating into the interior thereof and thereby initiating output current errors.

12 Claims, 3 Drawing Figures

AMPEROMETRIC GAS SENSOR, CATHODE ASSEMBLY THEREFOR AND METHOD OF MAKING SAID CATHODE ASSEMBLY

BACKGROUND OF THE INVENTION

Among presently used types of amperometric gas sensors are those which include a gas permeable membrane that is located at one end of an internal chamber filled with an electrolyte solution such as a solution of potassium chloride in water. Immersed in the electrolyte solution is a cathode electrode which is located in the vicinity of the membrane to maximize its exposure to gas molecules diffusing therethrough. Surrounding the cathode electrode is an anode electrode which completes the circuit through the electrolyte solution. these electrodes are connected to an external measuring instrument which supplies the operating voltage between the electrodes and which provides a user readable indication of the current flowing therebetween.

In gas sensors of the above-described type which sense oxygen the cathode electrode is usually a metal disc or cap, composed of a noble metal such as gold, which is attached to the end of a cathode mounting element or post. The interior of this post carries the conductor that connects the cathode electrode to the external instrument. During assembly, the cathode electrode is sealed to the end of the cathode mounting post with an epoxy cement. Thereafter, the interior of the cathode mounting post is filled with a suitable potting compound, which may also be an epoxy type material.

While cathode assemblies of the above-described type often operate satisfactorily at first, their performance frequently deteriorates with time, giving rise to residual currents, i.e., currents which bear no meaningful relationship to the quantity of gas diffusing through the membrane. This deterioration has required that gas sensors which include such cathode assemblies be carefully monitored and frequently calibrated. This need for monitoring and calibration has, in turn, increased the cost of operating amperometric gas sensors and has rendered them unsuitable for use in unattended installations.

During the making of the present invention it was discovered that one reason for the above-described deterioration in the migration or diffusion of the electrolyte solution into and through defects in the bonds formed by the cement that is used to seal the electrode to its mounting post. This migration of the electrolyte solution also occurs along defects in the bond between the sealing cement and the internal potting compound. It was also discovered that once this electrolyte solution reaches the vicinity of the inner surface of the cathode electrode, serious current measurement errors begin to occur. If, for example, the conductor to which the cathode electrode is soldered contains the usual mixture of tin and lead, the presence of the electrolyte solution will initiate electrochemical reactions therebetween that affect the potential of the cathode electrode. In addition, if the deterioration of the sealing cement progresses far enough, metal ions which have gone into solution as the result of these electrochemical reactions will diffuse back into and contaminate the electrolyte solution.

Additional problems have been found to occur as the result of the contact between inwardly leaked electrolyte solution and the thermistor assembly that is usually soldered to the inner surface of the cathode electrode to provide information about the cathode operating temperature. Certain of these problems occur as a result of the above-described electrochemical reactions between metals in the thermistor leads, the thermistor mounting saddle and the solder used to fasten the latter to the cathode electrode. The presence of the electrolyte solution in the vicinity of the thermistor can also give rise to still further errors by supporting the flow of leakage currents between the leads of the thermistor and by establishing unintended leakage paths between the thermistor and the cathode electrode. The latter leakage currents are particularly objectionable since they give the appearance of being genuine signal currents.

The above-described problems are aggravated by the fact that, during normal operation, the electrochemical reactions occurring at the outer surface of the cathode electrode cause hydroxyl ions to be present in the vicinity of the seals between the cathode electrode and the cathode mounting post. These ions have been found to attack these seals by reacting chemically with the epoxy compounds included therein. As a result, originally insignificant defects can be converted into defects that cause serious measurement errors. Moreover, even if the cathode assembly is originally without sealing defects, the presence of hydroxyl ions can produce such defects and thereby give rise to the above-described errors.

SUMMARY OF THE INVENTION

In accordance with the present invention, the above-described problems are eliminated by providing an improved electrode assembly which prevents the electrolyte solution from migrating into contact with the inner surface of the electrode element. Through the use of this improved electrode assembly, any defects which are present in the original seal between the electrode and the electrode mounting post are prevented from becoming leakage paths for the electrolyte. In addition, the reactive ions which are generated in the vicinity of the electrode during normal operation are prevented from aggravating defects in the electrode seals. As a result, gas sensors that are constructed in accordance with the present invention are not subject to the progressive deterioration tht is associated with the leakage of electrolyte in prior electrode assemblies. This, in turn, not only reduces the cost of maintaining the sensor, but also makes it possible to use the sensor in unattended installation where previously available gas sensors could not be used. While the following description is framed in terms of the cathode assembly of an amperometric oxygen sensor, it will be understood that the present invention is equally applicable to anode assemblies and to sensors for gases other than oxygen.

In the preferred embodiment of an oxygen sensor, the electrolyte solution is prevented from migrating into the interior of the cathode assembly by providing a water repellent electrochemically inert fluid filling in the space between the inner surface of the cathode electrode and the adjacent portion of the cathode mounting post. After the covering of this fluid with a suitable fluid barrier, the remainder of the cathode mounting post is then filled with a suitable potting compound. Because of its fluidity and immiscibility with the electrolyte solution, this fluid filling occupies and therefore prevents the electrolyte solution from entering any tiny cracks or defects which may be present in the seal between the cathode electrode and the cathode mounting post. This, in turn, prevents the appearance of the previously described measurement disturbing potentials on the cathode electrode. In addition, by virtue of its electrical nonconductivity, the fluid also prevents the flow of the above-described leakage currents between or from the thermistor leads. As a result, the performance of the cathode assembly of the invention does not deteriorate with time even in the presence of the hydroxl ions that are generated in the vicinity of the cathode during normal operation.

The preferred embodiment of the invention also contemplates the presence of a gas bubble or other compressible body in the above-described fluid filling. This compressible body acts as a pressure relief mechanism which protects the cathode assembly from the pressures that are incident to thermal expansion and contraction of the cathode electrode and its fluid filling during normal operation. This, in turn, prevents the rupture of the cathode seal as a result of substantial temperature changes in the environment of the gas sensor.

Among the many fluids that are suitable for practicing the present invention are silicone based oils such as those which contain dimethyl siloxane polymers. These oils are particularly desirable because of their low surface tension and high water repellancy. Other advantageous fluids include fluorinated oils, such as those sold under the trademark KRYTOX. Depending on the composition of the sealing material between the cathode electrode and the cathode mounting post, other filling fluids such as mineral oil may also be used. The chemical composition of the filling liquid is, however, not regarded as critical to the present invention, provided that the fluid exhibits the physical, electrical and chemical properties to be described hereinafter.

DESCRIPTION OF THE PREFERRED EMBODIMENTS

Figure 1:
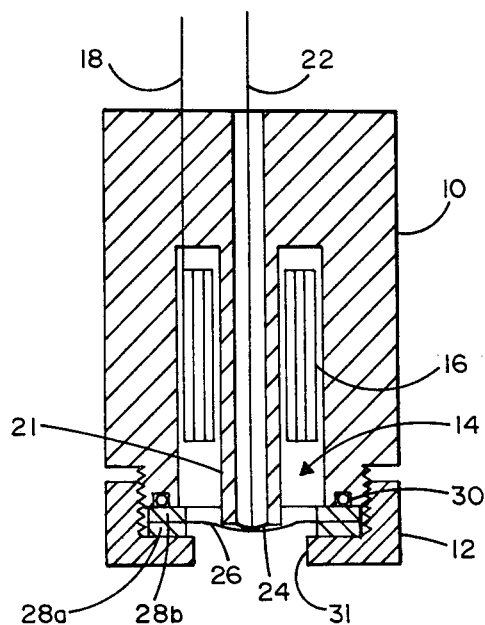
FIG. 1 is a cross-sectional view of a simplified amperometric gas sensor of a type known in the art.

Referring to FIG. 1, there is shown a simplified cross-sectional view of a known type of amperometric gas sensor, in this case an oxygen sensor. This sensor includes upper and lower housing sections 10 and 12, respectively, which may be made of a plastic material such as polyvinyl chloride. Housing sections 10 and 12 enclose a generally cylindrical electrolyte chamber 14 which is filled with a suitable electrolyte solution such as an aqueous solution of potassium chloride. Located within chamber 14 in an anode electrode 16 which may comprise a helically wound sheet of a metal such as silver and which may be connected to an external voltage source of a known type (not shown) through a lead 18. Also included within chamber 14 is a cathode assembly which includes cathode mounting element or post 21 and a conductor lead 22 through which the circuit including the above-mentioned voltage source is completed. The cathode assembly also includes a metallic cathode electrode 24 that typically comprises a rounded or dome-shaped metal disc of a noble metal such as gold the inner surface of which is soldered to lead 22.

Closing the lower end of electrolyte chamber 14 is a gas permeable membrane 26 that typically comprises a thin sheet of polytetrafluoroethylene which is supported in close proximity to cathode 24. This membrane may be mounted in any suitable manner, such as by being sealed between the two halves 28a and 28b of a compression ring assembly which is, in turn, sealed against the lower end of housing 10 by an O-ring 30 when housing section 12 is tightened against housing section 10.

The gas to be sampled through membrane 26 is applied to cathode 24 through an opening 31 in lower housing section 12. The component of interest, in this case oxygen, diffuses through membrane 26 and into the thin layer of electrolyte that is present between cathode 24 from membrane 26. Once in this thin layer of electrolyte, oxygen molecules are reduced to hydroxyl ions by electrons received from cathode 24. At the same time silver atoms are oxidized by yielding electrons to anode 16. The current that flows in conductors 18 and 22 as a result of these reactions is then used as a direct measure of the quantity of oxygen present.

Figure 2:
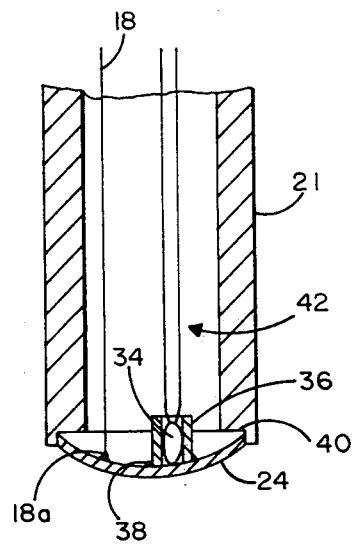
FIG. 2 is an enlarged fragmentary cross-sectional view of the end portion of a cathode assembly of a type known in the art.

Referring to FIG. 2, there is shown an enlarged cross-sectional view of the end section of the cathode assembly of the gas sensor of FIG. 1. Because of the larger scale of FIG. 2, there are illustrated therein certain additional structures which were left out of the cathode assembly of FIG. 1 for the sake of clarity. FIG. 2, for example, shows that a thermistor 34 is mounted in contact with the inner surface of cathode 24 to provide temperature information by which the final output reading may be accurately corrected for variations in the temperature at gas permeable membrane 26. Thermistor 34 is preferably held in place by crimping it within a metal annulus or saddle 36 which is soldered to the inner surface of cathode element 24, the resulting solder joints being illustrated as wedges such as wedge 38 of FIG. 2. Further information concerning the mounting of thermistor 34 is contained in U.S. Pat. No. 3,518,179 which issued in the name of T. M. Bleak et al. on June 30, 1970 and which is assigned to the assignee of the present application.

FIG. 2 also clearly shows that cathode 24 rests in a shallow circular recess 40 that is located at the end of mounting post 21. Not visible, because of its thinness, is a layer of epoxy cement which is present between cathode 24 and the inner surface of recess 40 and which is intended to provide a fluid-tight seal therebetween. During assembly, after the last mentioned seal is established, the empty interior space 42 within cathode mounting post 21 is filled with a suitable potting compound, which may be of any of a variety of well known types. The latter compound serves primarily to prevent the relative movement of the internal components of the cathode assembly.

Because of imperfections in the seal between cathode 24 and mounting post 21, as well as imperfections in the seal between the potting compound and the inner surface of cathode 24 and mounting post 21, there is a tendency for small quantities of the electrolyte solution in chamber 14 to gradually leak into the interior of the cathode assembly of FIG. 2. Because of its conductivity, this leaked electrolyte tends to promote electrochemical reactions between various ones of the metals in mounting saddle 36, the solder junctions, conductor 18 and the leads of thermistor 34. These reactions can cause substantial error potentials to appear on cathode 24. The potential of cathode 24 can, for example, be affected by the plating of one of the above metals on the inner surface of the cathode. The leaked electrolyte also promotes the flow of leakage currents both between the leads of thermistor 34 and between the latter and the cathode electrode. These potentials and leakage current have been found to give rise to serious errors in the measured oxygen concentration.

The above-mentioned problems are compounded by the fact that, during normal operation, the gas sensor of FIG. 1 generates hydroxyl ions in the vicinity of cathode 24. Over a period of time, these ions tend to chemically attack the seals of the cathode assembly, resulting in an increase in the leakage of the electrolyte solution into the interior thereof. This increase in leakage, in turn, causes the performance of the gas sensor to progressively deteriorate until ultimately it becomes totally unusable for making gas concentration measurements.

Figure 3:
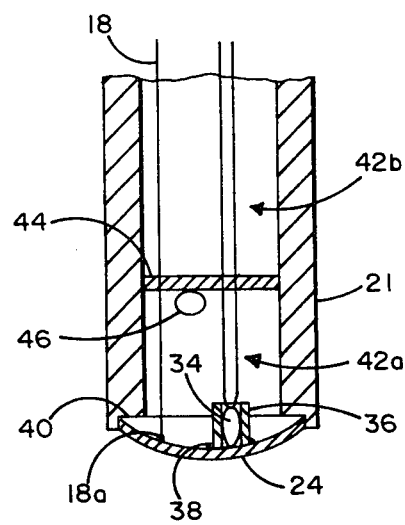
FIG. 3 is an enlarged fragmentary cross-sectional view of the end portion of a cathode assembly that is constructed in accordance with the the present invention.

Referring to FIG. 3, there is shown a cathode assembly which is similar to that shown in FIG. 2, like parts being similarly numbered, but which has been modified to include the features of the present invention. More particularly, the improved cathode assembly of FIG. 3 has been modified to include an end region 42a which is provided with a filling fluid (to be described more fully presently) which covers the circuit elements and connections in the vicinity of the inner surface of cathode electrode 24 and thereby protects the same from the above-described effects of leaked electrolyte solution. This fluid-filled end region is separated from the remainder 42b of the interior of the cathode assembly by a suitable liquid barrier 44 having a plurality of holes through which the leads of thermistor 34 and conductor 18 may be passed. Once liquid barrier 44 is in place, interior region 42b may be filled with a potting compound in the usual member to seal off the interior of the cathode assembly. It will be understood that as long as end region 42a is large enough to contain sufficient fluid to cover the circuit elements and connections on the inner surface of cathode 24, the relative sizes of regions 42a and 42b are of no significance to the practice of the present invention.

One important characteristic of the fluid used to fill end region 42a is that it be electrochemically inert, i.e., does not mediate oxidation-reduction reactions between the metals and compounds making up thermistor 34, mounting saddle 36, conductor 18, the various solder junctions and cathode 24. This characteristic assures that the filling fluid in region 42a does not permit the establishment of error potentials in the vicinity of cathode 24.

A second important characteristic of the filling fluid is that it be chemically inert, i.e., does not react with or dissolve any of the compounds making up mounting post 21, the epoxy seal in recess 40, fluid barrier 44, thermistor 34, as well as any of the above-mentioned metals. This characteristic assures that the cathode assembly will maintain its physical integrity even over periods of prolonged use.

A third important characteristic of the filling fluid in region 42a is that it be electrically nonconducting. This condition assures that no significant leakage currents can flow between the leads of thermistor 34, or between either of the leads of thermistor 34 and cathode 24 or anode 16. The absence of these leakage current, in turn, assures that the output of the oxygen sensor reflects only the flow of currents that are related to the oxygen content of the sample being monitored.

Other important characteristics of the filling fluid are water repellancy and low surface tension. Together these characteristics assure that the filling fluid will penetrate any tiny defects or cracks in the seal between cathode 24 and mounting post 22 and block the electrolyte solution from entering the same.

In spite of the number of required characteristics, a relatively large number of fluids are suitable for use in practicing the invention. One particularly desirable fluid is a silicone oil said under the designation Dow Corning 200, which is composed of a dimethyl siloxane polymer. This fluid is desirable because of its excellent wetting and water repellancy characteristics, its non-toxicity, and good adherency to plastic surfaces. Other examples of such fluids include a variety of fluorinated oils such as those sold under the trademark KRYTOX. More generally, subject only to the choice of a suitable cement for use in attaching cathode 24 to post 21, a large number of additional fluid, including mineral oil, are also usable. Fluids containing mixtures of any individually suitable fluids may also be used, provided that they do not react with one another. Thus, the fluid contemplated by the present invention is regarded as including all liquids except those which fail to exhibit one or more of the above-mentioned characteristics.

To the end that the pressures incident to the normal thermal expansions and contractions of the cathode assembly and its fluid filling are prevented from damaging the cathode assembly or the seal between cathode 24 and post 21, pressure relief means such as a gas bubble 46 is provided within cathode end region 42a. By contracting at high temperatures and expanding at low temperature, pressure relief bubble 46 effectively prevents pressures within region 42a from building up or falling to destructive values. While bubble 46 is a particularly inexpensive and convenient means for providing the desired pressure relief, it will be understood that any of a variety of other pressure relief structures such as elastomeric diaphragms and movable seals may be substituted for bubble 46.

In order to realize the full benefits of the invention, it is desirable that certain steps be taken during the construction of the gas sensor. It is important, for example, that the fluid filling be introduced into end region 42a without wetting the walls of that portion of the cathode mounting post which is to be located above fluid barrier 44. This non-wetting assures that a good seal will be established between post 21 and the potting compound that is later introduced into region 42b. One convenient may of introducing the fluid filling without producing this undesired wetting involves the use of a long needled syringe. After inserting the filled syringe deep within the interior of post 21 and discharging a measured quantity of fluid therefrom, the syringe is withdrawn carefully so as not to drip any fluid on the walls of the mounting post at any point above the surface of the just inserted fluid. Bubble 46 may then be introduced into the fluid either by injecting the fluid with a bubble from an air filled syringe, or by simply dropping a pre-measured gas-filled elastomeric sack onto the surface thereof.

Once the above-described steps have been taken, fluid barrier 44 may be inserted into post 21, after cathode lead 18 and the leads of thermistor 34 are threaded through respective holes therethrough. Thereafter, fluid barrier 44 is pushed into post 21 until it comes to rest on the surface of the fluid filling. Interior region 42b may then be potted in the usual manner to permanently seal the interior of the cathode assembly.

During the time that the potting compound is setting, the fluid filling in region 42a has ample time to diffuse into and occupy any tiny defects, such as pores and cracks, that may exist in the seal between cathode 24 and post 21. The water repellancy of this fluid and its retention in the defects by capillary action effectively prevents the electrolyte solution from entering these defects even after prolonged operation in the presence of the hydroxyl ions that are generated during the normal operation of the sensor. As a result, an oxygen electrode having the cathode assembly of the invention is free of the error potentials and leakage currents that have caused inaccuracies or failures in previously available oxygen electrodes. In addition, the oxygen electrode exhibits a substantial improvement in its useful life, thereby allowing the electrode to be used in applications such as unattended installations in which amperometric sensors have been considered unsuitable.

What is claimed is:

1. In an electrochemical gas sensor of the type having a gas permeable membrane, a housing defining an electrolyte chamber for receiving an electrolyte solution, an electrode, and an electrode mounting element for mounting the electrode in the electrolyte chamber in the vicinity of the gas permeable membrane, the improvement comprising:
    (a) a quantity of an electrochemically inert, electrically nonconductive fluid which is immiscible with the electrolyte solution,
    (b) means for sealing said quantity of fluid, within the electrode mounting element, in direct contact with the inner surface of the electrode,
    (c) whereby the electrolyte solution is substantially prevented from entering the mounting element and coming into contact with the inner surface of the electrode.

2. A gas sensor as set forth in claim 1 in which the inert fluid is selected from the group consisting of silicone oils, fluorinated oils and mineral oils.

3. A gas sensor as set forth in claim 1 including pressure-relief means for protecting the electrode from the pressures incident to the thermal expansion and contraction of the gas sensor.

4. A gas sensor as set forth in claim 1 in which the sealing means includes a fluid barrier for confining the fluid to the electrode end of the mounting element, and a potting compound for sealing the fluid barrier to the mounting element.

5. An electrode assembly for use in electrochemical gas sensors of the type having a gas permeable membrane and an electrolyte chamber containing an electrolyte solution, said electrode assembly being characterized by:
    (a) an electrode,
    (b) an electrode mounting element for supporting the electrode in the electrolyte chamber in the vicinity of the membrane,
    (c) a conductor within the mounting element for connecting the electrode in a remote measuring circuit,
    (d) an electrochemically inert, electrically insulating water repellant fluid,
    (e) means for sealing a body of said fluid within the electrode mounting element in direct contact with the inner surface of the electrode,
    (f) whereby said fluid covers the inner surface of the electrode and prevents the electrolyte solution from entering the electrode mounting element.

6. An electrode assembly as set forth in claim 5 in which said inert fluid contains a di-methyl siloxane polymer.

7. An electrode assembly as set forth in claim 5 in which said inert fluid contains a fluorinated oil.

8. An electrode assembly as set forth in claim 5 in which said inert fluid contains mineral oil.

9. A cathode assembly as set forth in claim 5 including pressure-relief means for protecting the electrode from the pressures incident to the thermal expansion and contraction of the electrode assembly.

10. A method for forming an electrode assembly for use in an electrochemical gas sensor of the type having a gas permeable membrane, an electrolyte chamber, and an electrode, said method including the steps of:
    (a) producing an electrode mounting element having an axial opening,
    (b) attaching a conductor to one side of the electrode,
    (c) glueing the electrode on one end of the mounting element to form a substantially fluid tight seal therewith, said conductor projecting into the axial opening of the mounting element,
    (d) injecting an electrochemically inert water repellant fluid into the axial opening to form a layer of fluid covering the inner surface of the electrode and the attached end of the conductor,
    (e) inserting a fluid barrier into the axial opening to cover said fluid layer, and
    (f) injecting a sealing compound into the axial opening to cover the fluid barrier and thereby seal the interior of the electrode assembly.

11. The method of claim 10 in which the inert fluid contains one or more of silicone oils, fluorinated oils, and mineral oils.

12. The method of claim 10 further including the step of introducing pressure-relief means into said layer of fluid before the insertion of the fluid barrier.

* * * * *